United States Patent [19]
Swartz

[11] 4,150,578
[45] Apr. 24, 1979

[54] APPARATUS FOR MEASURING EXCESS PORE WATER PRESSURE

[76] Inventor: Robert B. Swartz, 117 Oberlin Terr., Lansdale, Pa. 19446

[21] Appl. No.: 919,896

[22] Filed: Jun. 28, 1978

[51] Int. Cl.$^2$ .............................................. G01L 9/02
[52] U.S. Cl. ......................................... 73/725; 73/38; 73/170 A
[58] Field of Search ............... 73/717, 38, 170 A, 155, 73/725; 338/38

[56] References Cited

U.S. PATENT DOCUMENTS

| | | | |
|---|---|---|---|
| 3,534,605 | 10/1970 | Koning et al. | 73/170 A |
| 3,935,745 | 2/1976 | Jonell et al. | 73/704 |
| 3,990,310 | 11/1976 | Greer et al. | 338/38 |

Primary Examiner—Donald O. Woodiel
Attorney, Agent, or Firm—Seidel, Gonda, Goldhammer & Panitch

[57] ABSTRACT

An elongated tubular housing has differential pressure transducers at spaced points therealong and electrically insulated therefrom by a mounting means. Each mounting means has a diaphragm exposed to pore water pressure and a diaphragm exposed to hydrostatic pressure at its location. The opposite sides of a third diaphragm are responsive to the pore water pressure and hydrostatic pressure. Conductors are provided on opposite sides of the third diaphragm to measure differential conductance which is analogous to excess pore water pressure.

9 Claims, 5 Drawing Figures

APPARATUS FOR MEASURING EXCESS PORE WATER PRESSURE

BACKGROUND

A device for measuring pore water pressure is known. For example, see U.S. Pat. No. 3,935,745.

SUMMARY OF THE INVENTION

The present invention is directed to apparatus for measuring the difference between hydrostatic pressure and pore water pressure in sediment of oceans, seas and the like. The apparatus includes an elongated tubular housing having a pointed tip at one end for introduction into the sediment. Differential pressure transducers are provided in the housing. The transducers are supported at predetermined spaced locations by electrically insulated mounting means. Each mounting means has an inlet for transmitting pore water pressure at each of said locations. Each transducer mounting means has a first diaphragm exposed to the pore water pressure at its location. Each transducer mounting means also has a second diaphragm exposed to the hydrostatic pressure in said tubing at its location.

Each transducer has discrete chambers on opposite sides of a third diaphragm. A portion of each chamber is spaced from the third diaphragm by a narrow gap. One side of the third diaphragm contains an electrolyte insulated from and responsive to said hydrostatic pressure. The other side of the third diaphragm contains an electrolyte insulated from and responsive to pore water pressure. A discrete electrical wire conductor is provided in each of said chambers on opposite sides of said third diaphragm for measuring the differential pressure.

It is an object of the present invention to provide novel apparatus for measuring excess pore water pressure and other soil properties such as soil shear strength in a manner whereby the device is smaller in size, simple, and without the need for electronic components and at the same time being reliable. The device is also capable of accurately measuring very small differential pressures at very large ambient pressures.

For the purpose of illustrating the invention, there is shown in the drawings a form which is presently preferred; it being understood, however that this invention is not limited to the precise arrangements and instrumentalities shown.

Figure 2:
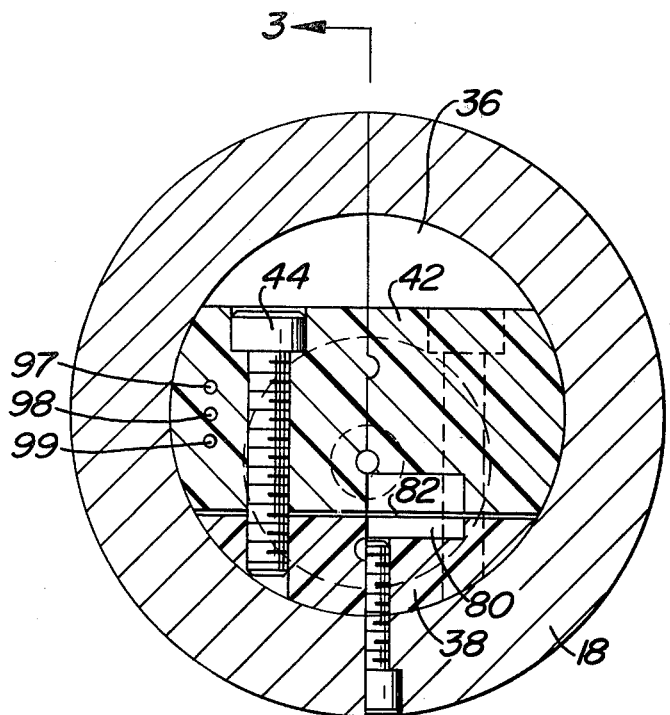
FIG. 2 is a sectional view taken across the apparatus in FIG. 1.

Referring to the drawings in detail, wherein like numerals indicate like elements, there is shown apparatus in accordance with the present invention for measuring excess pore water pressure which may have been caused in ocean or sea sediment by soil consolidation, landslides, wave action, gas pockets, chemical reactions, etc.

The apparatus 10 includes a tubular housing of stainless steel or the like having an outer diameter of about 1¼ inches. The housing has a tip 12 threadedly coupled to a pressure module 14. A cone penetrometer or some other transducer may be mounted in tip 12. Tip 12 could be the penetrometer which is a type of load cell for measuring soil shear strength. Module 14 is threadedly coupled to a spacer module 16 which in turn is threadedly coupled to a pressure module 18 which in turn is threadedly connected to a spacer module 20, etc. Each module is sealed to the next adjacent module by means of an O ring or the like.

Figure 1:
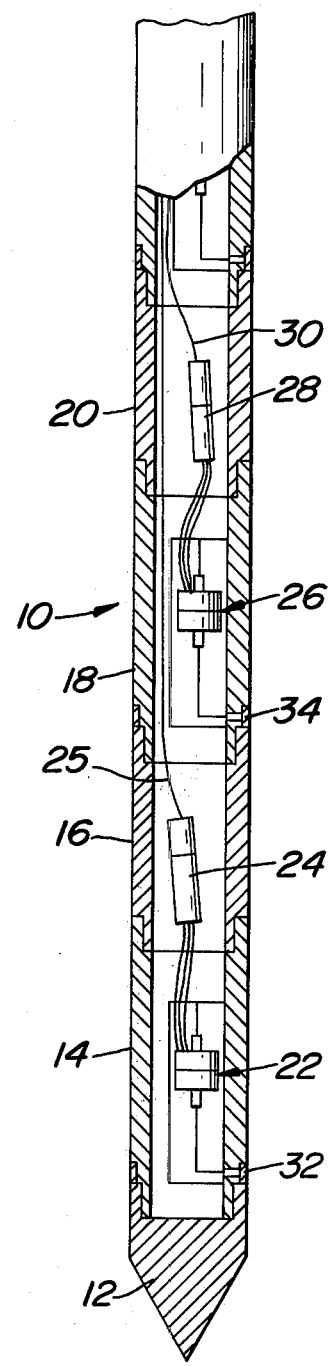
FIG. 1 is a vertical sectional view of the emergent end of apparatus in accordance with the present invention.

As shown more clearly in FIG. 1, a transducer 22 is provided within module 14. Transducer 22 is connected to an electrical connector in spacer 16. Connector 24 is connected to an electrical conductor conduit 25 extending to a surface instrument. A transducer 26 is disposed within module 18 and is connected to a connector 28 in spacer module 20. Connector 28 is connected to a conductor conduit 30 extending to said surface instrument. The pattern is repeated along the length of the apparatus 10. A filter 32 is provided associated with an inlet for pore water pressure to the transducer 22. A filter 34 is provided in connection with an inlet for pore water pressure to the transducer 26. Each of the transducers is spaced from the inner peripheral surface of the tubular housing so as to define a wire-way 36 for accommodating the conductor conduits 25, 30, etc.

Figure 3:
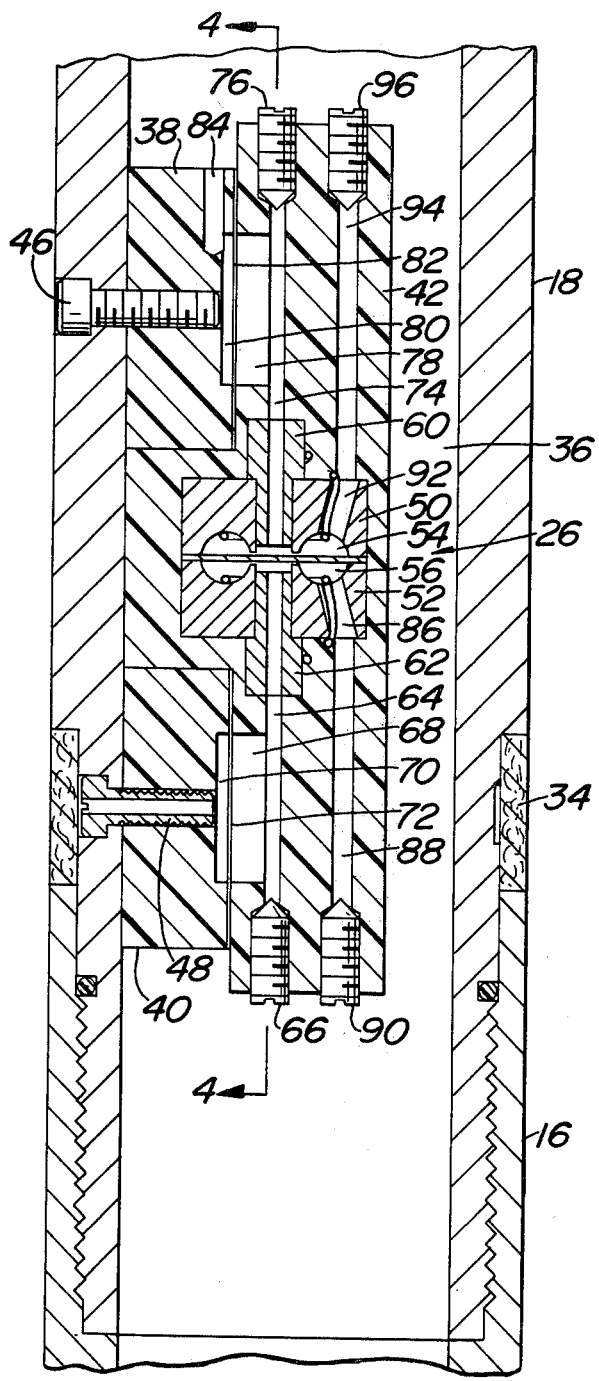
FIG. 3 is an enlarged vertical sectional view of one transducer as seen along the line 3—3 in FIG. 2.
Figure 4:
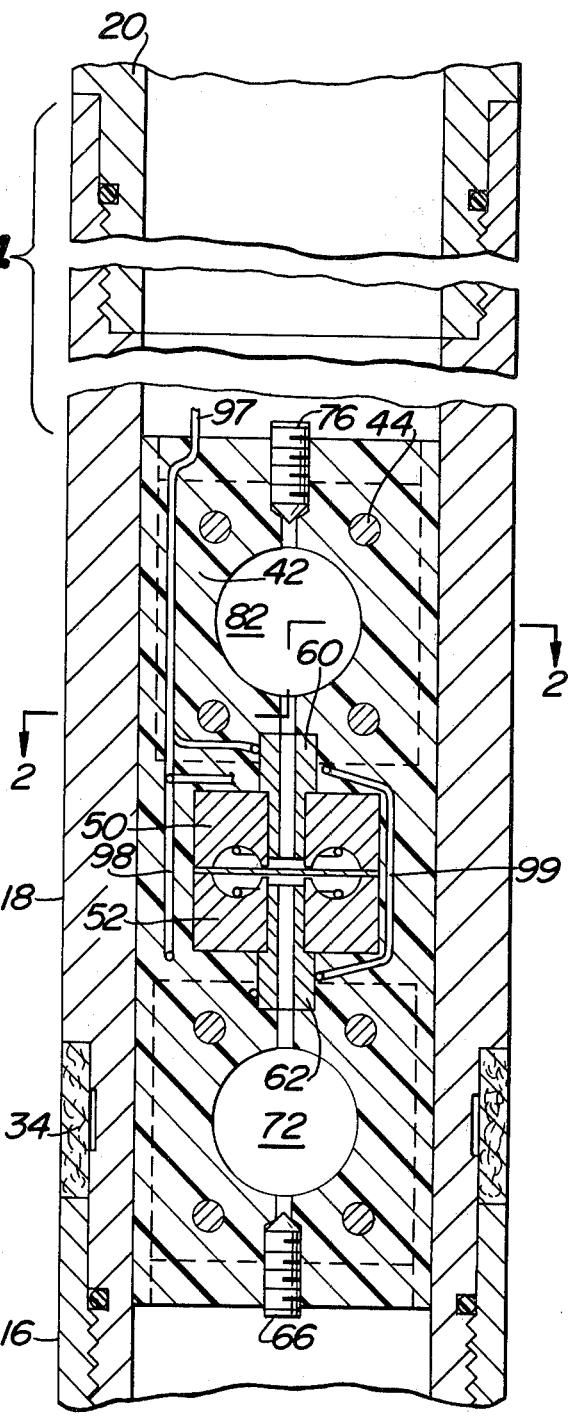
FIG. 4 is a sectional view taken along the line 4—4 in FIG. 3.

Each of the pressure modules is identical. Hence, only pressure module 18 will be described in detail. Referring to FIGS. 2 and 3, the transducer 26 is supported within the tubular housing by a mounting means comprised of anchor segments 38 and 40. The segments 38 and 40 are of an electrically non-conductive material such as any one of a wide variety of polymeric plastics. Segment 38 is bolted to the pressure module 18 by a bolt 46. Segment 40 is bolted to the module 18 by a bolt 48. Bolt 48 is hollow and at one end communicating with the surrounding pore water pressure by way of the filter 34. See FIG. 3.

A matrix 42 of an electrically non-conductive potting material is bolted to each of the segments 38, 40 by way of a plurality of bolts 44. Four such bolts 44 are illustrated in connection with each of the segments 38, 40. A lesser number of bolts 44 may be provided or any other equivalent fastener may be used. It will be noted that the matrix 42 has a flat on one side so as to define the wire-way 36. See FIGS. 2 and 3.

Figure 5:
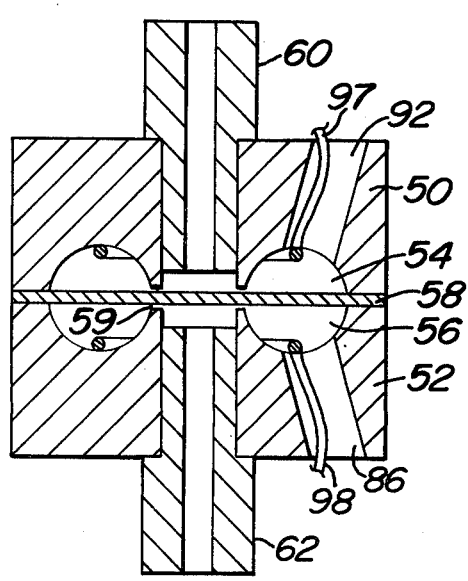
FIG. 5 is an enlarged detail view of a portion of the transducer as shown in FIG. 3.

Referring to FIGS. 3 and 5, the transducer 26 includes cylinders 50 and 52 made from a material such as quartz. On an end face of cylinder 50, there is provided an annular cavity 54. On a mating end face of cylinder 52, there is provided an annular cavity 56. A diaphragm 58 from a material such as quartz is adhesively bonded to the juxtaposed end faces of the cylinders 50, 52. Adjacent the axis of the cylinders 50, 52, the cavities are spaced from the diaphragm 58 by an annular gap 59.

An electrode 60 made from a material such as silver is axially disposed within the cylinder 50 and has a center bore communicating with the cavity 54 by way of the gap 59. Cylinder 52 is provided with an axially disposed electrode 62 of a material such as silver. Electrode 62 has an axial bore communicating with cavity 56 by way of the gap 59.

The matrix 42 has a cylindrical passage 64 aligned with the bore in electrode 62. At the free end, passage 64 is closed by a threaded plug 66. Matrix 42 has a chamber 68 communicating directly with passage 64. The anchor segment 40 has a chamber 70 corresponding in size to the size of chamber 68. A diaphragm 72 extends across chambers 68, 70 and is secured between matrix 42 and the end face of segment 40. Pore water enters filter 34, through the hollow bolt 48, and fills the chamber 70. Chamber 68, passage 64, and cavity 56 are filled with an electrolyte such as salt water. Since the electrolyte is a known amount of liquid which is a closed system and lacking any gas, the pressure in cavity 56 is directly responsive to the pressure in chamber 70.

The matrix 42 has a cylindrical passage 74 in alignment with the bore of electrode 60. The free end of passage 74 is closed by a threaded plug 76. A chamber 78 is provided in the matrix 42 coextensive with the passage 74. A chamber 80 is provided in the anchor segment 38 coextensive with the chamber 78. A diaphragm 82 extends across the chambers 78, 80 and is fixedly secured between the matrix 42 and the juxtaposed face of anchor segment 38. The diaphragms 72, 82 are identical. The size of chambers 68, 70, 78, 80 are identical. Another segment 38 is provided with a passage 84 for communicating hydrostatic pressure within the module 18 to one side of the diaphragm 82. Chamber 78, passage 74, and cavity 54 are a closed system filled with an electrolyte such as salt water. Thus, the pressure in cavity 54 is directly responsive to the hydrostatic pressure at the location of module 18.

Cylinder 52 has a passage 86 communicating at one end with cavity 56 and at its other end with a cylindrical passage 88 in the matrix 42. Passage 88 is closed by a threaded plug 90.

Cylindrer 50 is provided with a passage 92 communicating at one end with cavity 54 and at its other end with a cylindrical passage 94 in the matrix 42. A threaded plug 96 closes one end of the passage 94. Threaded plugs 66, 76, 90 and 96 are made from electrically non-conducting material.

Three conductors designated 97, 98 and 99 extend through the matrix 42. See FIG. 2. Conductor 97 is the hydrostatic conductor since it extends into the cavity 54 by way of passage 92. Conductor 98 is the pore conductor since it extends into the cavity 56 by way of the passage 86. Within cavity 54, conductor 97 terminates in a loop coaxial with the cavity. Likewise, conductor 98 terminates in a loop within and coaxial with the cavity 56. Conductor 99 is a common conductor and therefore is metallurgically bonded to each of the electrodes 60, 62.

The apparatus 10 is used as follows. The housing is placed with its pointed tip 12 or other transducer in contact with sediment. Pressure is applied to the other end of the housing to force the housing into the sediment. The conductors 97, 98 and 99 from each transducer are connected via conduit 30 to a surface instrument such as a Wheatstone bridge in a conventional manner. At each of the transducers, diaphragm 58 is responsive by way of a discrete closed system of an electrolyte to the hydrostatic pressure and the pore water pressure. If, for example, the pressure in cavity 56 exceeds the pressure in cavity 54, diaphragm 58 will move toward the electrode 60 thereby decreasing the conductance gap in cavity 54 and enlarging the conductance gap 59 in cavity 56. This causes an increased electrical resistance across the gap in cavity 54 measured between electrodes 97 and 99, and a decrease across the gap 59 in cavity 56 measured between electrodes 98 and 99. The changes in resistance are monitored as the output voltage of the Wheatstone bridge. The output voltages may be translated as a direct analogy to excess pore water pressure at different levels in the sediment corresponding to the locations of the transducers 22, 26, etc.

The plugs 76, 96 facilitate filling the passages 74, 94 and the cavity 54 with the electrolyte and to purge any gases from the electrolyte. The plugs 66, 90 perform a similar function. Since the entire transducer is completely filled with liquid, it is inherently adaptable to the accurate measurement of pore pressures at very high ambient pressures with very small fluid flow. The diaphragm 58 of each transducer is preferably made from a material such as quartz so as to minimize temperature differentials, zero point shift and any elastic hysteresis effect whereby a totally linear relationship will exist between the pore water pressure and the electrical output of the transducer. The electrical excitation of the Wheatstone bridge circuit is expected to be a high frequency AC signal in the range of 2–10 kHz. The frequency is set at a value which achieves a totally resistive impedance for the transducer. The excitation should not contain any net DC voltage which would tend to electrolyze the solution and liberate molecular chlorine at one of the electrodes and metallic sodium at the other.

The quartz diaphragm 58 of the differential conductance transducer 26 can be treated as a circular plate of uniform thickness with rigid supports on its circumference and a uniformly applied load ($\Delta P$). Suitable formulas are:

$$(\text{defection}) = Y\,\text{max.} = (K\,W\,a^2)/(E\,t^3)$$

where:
$K$ = Coefficient = 0.053
$W$ = Plating loading = $\Delta P\,\pi a^2$
$a = r = d/2$ = radius of plate
$t$ = diaphragm thickness
$E$ = Modulus of Elasticity $$(\text{stress})\quad S\,\text{max} = (K_1\,W)/t^2$$

where: $K_1$ = Coefficient = 0.239

Into the above equations, substitute the following values to calculate $\Delta P$ vs $Y$ max for a specific transducer which is presented here as an example:
$E = 11.1 \times 10^6$ PSI (fused quartz)
$a = r = d/2 = 0.25''$
$t$ = variable
$W$ = variable = $\Delta P$
substitute, $$Y\,\text{max} = \frac{(0.53)(\Delta P)\pi(.25)^2(.25)^2}{(11.1 \times 10^6)t^3}\,\text{inches} \quad (1)$$

or, $$Y\,\text{max} = (5.859455 \times 10^{-11})\frac{\Delta P}{t^3}$$

and, $$S\,\text{max} = \frac{.239(\Delta P)\pi(.25)^2}{t^2}\,\text{PSI}$$

or, $$S\,\text{max} = (.0469275)\frac{\Delta P}{t^2}$$

From equation (1), one can plot a curve of $Y$ max as a function of $\Delta P$ for each substituted value of $t$.

To determine stress vs $\Delta P$, $t$, and $Y$ max, apply the above relationships as follows:

$$S\,\text{max} = A\frac{\Delta P}{t^2} \quad Y\,\text{max} = B\frac{\Delta P}{t^3}$$

where: $A = 0.0469275 =$ and $B = 5.859455 \times 10^{-11}$

Substituting for t in the above, $$S\ max = \frac{A(\Delta P)}{\left(\frac{B\ \Delta P}{Y\ max}\right)^{2/3}} = K_2(\Delta P)^{1/3}(Y\ max)^{2/3}$$

where: $K_2 = A/B^{2/3}$ or, $$Y\ max = [K(\Delta P)^{1/3}]^{-3/2}\ (S\ max)^{3/2}$$
$$= (K_2)^{-3/2}\ (\Delta P)^{-1/2}\ (S\ max)^{3/2}$$
$$= K_3\ (S\ max)^{3/2}\ (\Delta P)^{-1/2}$$

Where:

$$K_3 = (K_2)^{-3/2} = \left[\frac{.0469275}{(5.859455 \times 10^{-11})^{2/3}}\right]^{-3/2}$$

$K_3 = 5.76395 \times 10^{-9}$

Therefore $$Y\ max = \frac{5.76395 \times 10^{-9}}{\sqrt{\Delta P}}\ (S\ max)^{3/2} \quad (2)$$

From equation (2), insert values for S max and achieve a series of relationships with Y max as a function of $\Delta P$ (or lines of constant S max). Superimposing these curves on those obtained from equation (1) yields a plot to be used for selection of diaphragm thickness and transducer range.

When filled with salt solution, the cavities 54, 56 become a resistive element with the majority (>80%) of its resistance contained in the narrow gap between the center electrode hole in the conductance cell and the outer annular chamber.

The resistance of the conductance gap can be calculated using the standard equation:

$$R = \rho(l/A)$$

where:
R = Total resistance of element
$\rho$ = Resistivity of medium (ohm - in)
l = length of element in direction of current flow
A = cross-sectional area of element perpendicular to flow where for the same specific transducer as before:
cg = thickness of gap = 0.0005 inches
d = ID of hole in cylinders 50 and 52 = 0.125 inches
W = radial width of gap = 0.020 inches In the conductance transducer, $l = w = .020$ inches $A \cong (d + \frac{w}{2} + \frac{w}{2})\pi(Cg)\ in.^2$ $\cong (.125 + \frac{.020}{2} + \frac{.020}{2})\pi(.0005)$ $\cong 2.277 \times 10^{-4}\ in^2$ Choosing an electrolyte with a conductance similar to sea water, $\rho = 34.84$ ohm - cm $$Rcg = \frac{34.84}{2.54} \times \frac{.020}{2.277 \times 10^{-4}} = 1205\ ohms$$

The cells of the transducer are connected as series legs of a Wheatstone bridge as before, $$R = \rho(l/A)$$

where
l = w
$A = (d+w)\pi(Cg)$
$Cg = g \pm y$
g = Ambient conductance gap opening
y = Diaphragm deflection (Y max = Constant $X\Delta P$)

Assuming $P_2 > P_1$ $Cg_1 = g - y$ $Cg_2 = g + y$ where:
$P_2$ = Pore water pressure
$P_1$ = Hyrostatic pressure
$Cg_1$ = Hydrostatic conductance gap
$Cg_2$ = Pore water conductance gap therefore $$Rg_1 = \rho\frac{w}{\pi(d+w)(g-y)} \quad (3)$$

where: $Rg_1$ = Resistance of hydrostatic gap and $$Rg_2 = \rho\frac{w}{\pi(d+w)(g+y)} \quad (4)$$

where: $Rg_2$ = Resistance of pore water gap

The output of the bridge circuit can be expressed as, $$\frac{V_1 - V_2}{E} = \frac{\text{Volts output}}{\text{Volts applied}}$$

where:
$V_1$ = potential between $Rg_1$ and $Rg_2$
$V_2$ = potential between constant legs of bridge circuit In order to calculate the above expression, apply Ohms law to the bridge circuit:

$V_1 = i_1 Rg_1$ and $E = i_1\ (Rg_1 + Rg_2)$ dividing yields, $$\frac{V_1}{E} = \frac{Rg_1}{Rg_1 + Rg_2} \quad (5)$$

A similar computation yields, $$\frac{V_2}{E} = \frac{R_1}{R_1 + R_2}\ (= \text{constant}) \quad (6)$$

where: $R_1$ and $R_2$ are constant legs of bridge circuit

Subtracting (6) from (5), $$\frac{V_1 - V_2}{E} = \frac{Rg_1}{Rg_1 + Rg_2} - \frac{R_1}{R_1 + R_2} \quad (7)$$

Substituting the expressions (3) and (4) into (7) and reducing, (7) becomes $$\frac{V_1 - V_2}{E} = \frac{g+y}{2g} - \frac{R_1}{R_1 + R_2} \quad (8)$$

When operating at "0" PSID, the bridge will be balanced, i.e., $V_1=V_2$, $Rg_1=Rg_2$, and $R_1=R_2$ by symmetry of fabrication.

Expression (8) now reduces to $$\frac{V_1 - V_2}{E} = \frac{y}{2g} \quad (9)$$

Equation (1) describes the relationship between applied differential pore pressure and diaphragm deflection, $$Y = (5.859 \times 10^{-11}) \frac{\Delta P}{t^3} \quad (1)$$

Substituting (1) into (9) yields $$\frac{\Delta V}{E} = \frac{5.859 \times 10^{-11}}{2g \, t^3} \Delta P \quad (10)$$

For any given transducer t and g are constant (diaphragm thickness and ambient conductance gap) and (10) becomes $$\Delta V/E = \text{constant} \cdot \Delta P \quad (11)$$

The present invention may be embodied in other specific forms without departing from the spirit or essential attributes thereof and, accordingly, reference should be made to the appended claims, rather than to the foregoing specification as indicating the scope of the invention.

It is claimed:

1. Apparatus for measuring excess pore water pressure in ocean sediments and the like comprising:
   (a) an elongated tubular housing having a pointed tip adapted to enter a sediment,
   (b) differential pressure transducers in said housing, said transducers being supported at predetermined spaced locations by electrically insulated mounting means, each mounting means having an inlet for transmitting pore water pressure at each of said locations, each mounting means having a first diaphragm adapted to be exposed to the pore water pressure at its location, each mounting means having a second diaphragm exposed to the hydrostatic pressure in said tubing at its location,
   (c) each transducer having discrete chambers, said chambers being on opposite sides of a third diaphragm, a portion of each chamber being spaced from said third diaphragm by a narrow gap, one side of said third diaphragm containing an electrolyte isolated from and responsive to said hydrostatic pressure on said second diaphragm, the other side of the third diaphragm containing an electrolyte isolated from and responsive to pore water pressure on said first diaphragm, and discrete electrical wire conductors, one of said conductors being in one of said chambers, another of said conductors being in the other of said chambers, and a third of said conductors being a common conductor connected to a pair of electrodes with each electrode being exposed to one side of said third diaphragm.

2. Apparatus in accordance with claim 1 wherein the mounting means having said first diaphragm includes a hollow fastener for securing the mounting means to the tubular housing and for transmitting pore pressure to said first diaphragm, the exposed surface of said first and second diaphragms being equal.

3. Apparatus in accordance with claim 1 wherein each transducer has a surface spaced from the inner periphery of said housing to define a wire-way for conductors associated with a transducer therebelow or other transducers such as a cone penetrometer which would be interface with this invention and used in place of the pointed tip specified in claim 1(a) above.

4. Apparatus in accordance with claim 1 wherein said discrete chambers on opposite sides of said third diaphragm are annular and coaxial, with the conductor in each of said chambers being in the form of a loop.

5. Apparatus in accordance with claim 1 wherein said mounting includes an anchor segment secured to the inner surface of said housing and having a flat surface facing the longitudinal axis of said housing, each transducer including an electrically nonconductive matrix secured to its respective anchor segment.

6. Apparatus in accordance with claim 5 wherein said segment flat surface supports said first diaphragm and has a cavity covered by the first diaphragm.

7. Apparatus in accordance with claim 5 wherein said segment flat surface supports said second diaphragm and has a cavity covered by the second diaphragm.

8. Apparatus for measuring pressure in ocean sediments and the like comprising:
   (a) an elongated tubular housing having a pointed tip adapted to enter a sediment,
   (b) differential pressure transducers in said housing, said transducers being supported at predetermined spaced locations by electrically insulated mounting means, each mounting means having an inlet for transmitting pressure at each of said locations, each mounting means having a first diaphragm adapted to be exposed to the pressure at its location, each mounting means having a second diaphragm exposed to the hydrostatic pressure in said tubing at its location,
   (c) each transducer having discrete chambers, said chambers being on opposite sides of a third diaphragm, a portion of each chamber being spaced from said third diaphragm by a narrow gap, one side of said third diaphragm being responsive to said hydrostatic pressure on said second diaphragm, the other side of the third diaphragm being responsive to pressure on said first diaphragm, and electrical wire means for measuring differential conductance in said chambers and transmitting a signal upwardly through the housing to a surface instrument.

9. Apparatus in accordance with claim 8 wherein said tip includes a cone penetrometer.

* * * * *